United States Patent [19]
Brown

[11] 4,316,984
[45] Feb. 23, 1982

[54] THERMOLABILE ACUTANCE DYES

[75] Inventor: Harvey A. Brown, Lake Elmo, Minn.

[73] Assignee: Minnesota Mining and Manufacturing Company, St. Paul, Minn.

[21] Appl. No.: 163,528

[22] Filed: Jun. 27, 1980

Related U.S. Application Data

[62] Division of Ser. No. 964,480, Nov. 29, 1978, Pat. No. 4,260,676.

[51] Int. Cl.$^3$ .......... C07D 215/12

[52] U.S. Cl. .......... 546/165; 542/400; 542/468; 548/121; 548/152; 548/178; 548/179; 548/217; 548/330

[58] Field of Search .......... 546/165; 542/468, 400; 548/217, 152, 178, 179, 121, 330

[56] References Cited

U.S. PATENT DOCUMENTS

| | | | |
|---|---|---|---|
| 3,988,156 | 10/1976 | Sturmer | 96/84 R |
| 4,028,113 | 6/1977 | Sturmer | 96/84 R |
| 4,033,948 | 7/1977 | Brown | 542/400 |
| 4,088,497 | 5/1978 | Brown | 96/114.1 |
| 4,153,463 | 5/1979 | Lea | 96/114.1 |
| 4,184,871 | 1/1980 | Oba et al. | 542/468 |

OTHER PUBLICATIONS

Van Allen et al., Chem. Abst. 83 (1975) #81171b.

*Primary Examiner*—Arthur P. Demers
*Attorney, Agent, or Firm*—Cruzan Alexander; Donald M. Sell; Mark A. Litman

[57] ABSTRACT

A particular class of novel nitro-substituted dyes has been found to act as effective, heat labile acutance dyes for photothermographic emulsions.

6 Claims, No Drawings

THERMOLABILE ACUTANCE DYES

This is a division of application Ser. No. 964,480, filed Nov. 29, 1978, now U.S. Pat. No. 4,260,676.

This invention relates to compounds suitable for use as acutance dyes in photosensitive compositions, to the preparation of such compounds and to photosensitive compositions containing the compounds. The invention is particularly concerned with photothermographic compositions of the type known as "dry silver" compositions.

Dry silver photosensitive compositions comprise an intimate mixture of a light-sensitive silver halide and another silver compound such as a silver salt of an organic acid, e.g., silver behenate or silver saccharine. The organic silver salt is substantially light-insensitive and, upon reduction, gives a visible change. Such a mixture is usually prepared in suspension and the resulting dispersion spread as a layer on a suitable substrate. When dry, the layer is exposed to a light image and thereafter a reproduction of the image can be developed by heating the layer in the presence of a reducing agent for silver ions such as hydroquinone or certain substituted phenols.

It is because the exposure and development of the layer occur without using an externally applied developer solution, such as conventional aqueous solutions, that these materials are often referred to as dry silver light-sensitive materials. Such materials in which minor amounts of a photosensitive silver halide catalyst-progenitor (the catalyst being photoinduced silver) are associated in catalytic proximity with major amounts of a heat sensitive oxidation-reduction image forming reaction mixture which reacts more rapidly in the presence of the catalyst resulting upon exposure of the silver halide are well known in the art. Examples of such materials are described in British Pat. No. 1,110,046 and in U.S. Pat. Nos. 3,839,049 and 3,457,075.

We believe that when the mixture is exposed to light a latent image of silver is formed in the silver halide. Thereafter, the organic silver compound can be reduced by heating in the presence of the reducing agent, this reduction being catalyzed image-wise by the light exposed silver halide. By a suitable choice of temperature, the reduction of the silver compound can be catalyzed in the light exposed areas to give a visible darkening while any slight reduction which occurs in the non-light exposed areas is insufficient to give a marked change. Because the silver halide acts as a catalyst-progenitor, very small amounts of it can suffice, e.g., 0.1 to 10% by weight of the mixture. However, large amounts, e.g., up to 15 or even 20%, may be desirable in some circumstances.

To improve the sharpness or definition of photographic images, a dye known as an acutance dye is often incorporated into photosensitive compositions. To be effective, the acutance dye will absorb at wavelengths at which the photosensitive composition is sensitive. The longer the path length of the light in the layer of light sensitive composition, the greater the attenuation. Therefore, scattered light is attenuated or absorbed to a larger extent than light which impinges directly on a light sensitive crystal. As a result, although the overall speed of the composition is reduced slightly, scattered light and other light rays which are liable to produce a blurred image are preferentially absorbed. The overall definition and sharpness of images produced in the layer thus are increased.

An acutance dye for use in a dry silver composition is preferably heat labile, that is to say, it is decomposed or converted by the heat development of the dry silver composition to one or more compounds which are colorless.

It is therefore an object of this invention to provide dry silver compositions with acutance dyes which absorb light at at least some of those wavelengths to which the composition is sensitive and which are rendered essentially colorless upon heat development of the dry silver composition.

According to this invention there is provided a light-sensitive composition comprising an intimate mixture of a substantially light-insensitive silver compound which upon reduction gives a visible change, silver halide to provide a catalyst for this reduction, a reducing agent for silver ions, and, as an acutance dye, a compound in accordance with that part of the invention hereinafter described.

According to the invention there is also provided a compound having the general formula:

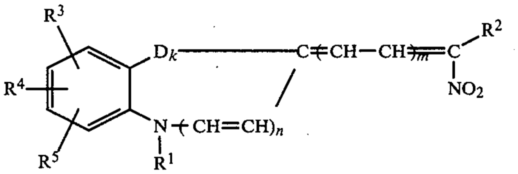
(I)

in which $R^1$ represents an alkyl group containing 1 to 12 carbon atoms, generally 1 to 8 carbon atoms and more usually 1 to 4 carbon atoms, $R^2$ represents the group

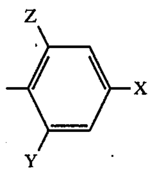

wherein X, Y and Z are independently selected from the group of H, $NO_2$, CN, perfluoroalkyl of 1 to 4 carbon atoms, and halogen with the proviso that at least one of X, Y, and Z is $NO_2$. Preferably neither X nor Y is H. Most preferably X, Y and Z are combinations of $NO_2$ and CN or both are $NO_2$. Each of $R^3$, $R^4$ and $R^5$ independently represent a substituent which, as known in the art, can be present in a cyanine dye type heterocyclic nucleus, D represents —CH=CH, O, >$NR^7$, >$C(CH_3)_2$, —S— or —Se—, $R^7$ represents an alkyl group containing 1 to 4 carbon atoms or $CH_3CO$—, n is 1 when k is 0 or k is 1 when n is 0, and m is 0, 1, 2 or 3.

The more preferred dyes of the invention are represented by the formula:

(II)

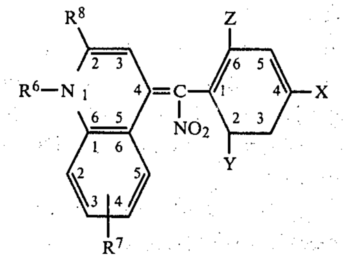

wherein

X, Y and Z are selected from the group of H, $NO_2$, CN, perfluoroalkyl of 1 to 4 carbon atoms, and halogen, with the proviso that at least one of X, Y and Z is $NO_2$. Preferably neither X nor Y is H, and most preferably X and Y are $NO_2$ or CN, especially the case where both X and Y are $NO_2$, $R^6$ is alkyl of 1 to 12 carbon atoms, preferably 1 to 8 carbon atoms, and most preferably 1 to 4 carbon atoms, $R^7$ is any quinoline dye substituent, preferably alkyl, alkoxy, halogen, $NO_2$, or aryl, and most preferably alkyl or alkoxy of 1 to 4 carbon atoms. There may be more than one $R^7$ group on the quinoline nucleus, and $R^8$ is H, or alkyl or alkoxy of 1 to 8 carbon atoms, most preferably H or alkyl or alkoxy of 1 to 3 carbon atoms.

The substitution of the quinoline portion of the dyes of the present invention is known in the art as shown in DT (W. German) No. 2,242,761.

The substituents $R^3$, $R^4$, and $R^5$ (and $R^7$) may be the same as or different from one another and each represents a substituent which can be present in a cyanine dye type heterocyclic nucleus. Such substituents are known in the art and include hydrogen or halogen, e.g., chlorine, bromine or iodine, an alkyl or alkoxy group containing 1 to 4 carbon atoms, an alkenyl group containing 2 to 4 carbon atoms, $-(CH_2)_pCOOH$ where p is 0, 1, 2 or 3, $-NO_2$, $-NH_2$, or $-NHCOCH_3$, or any two adjacent groups of $R^3$ to $R^5$ together represent the carbon atoms needed to complete a fused on benzene ring. Preferably at least one, more preferably at least two, of the substituents $R^3$ to $R^5$ represent hydrogen atoms. The most preferred substituents to be represented by each of $R^3$ to $R^5$ are hydrogen, chlorine or bromine atoms, or methyl, ethyl, methoxy or ethoxy groups.

It is found that dry silver compositions containing one of the above noted acutance dyes can give excellent sharp images and that the actuance dye will be rendered essentially colorless by the heating required to develop the composition. This is unexpected in view of the fact that many of these dyes are found not to be decomposed to a colorless state when they are heated on their own to the temperature at which the dry silver compositions are heated for development.

The acutance dyes can be incorporated into the dry silver compositions of the invention in an amount from $5\times10^{-4}$ to 0.1 mole of acutance dye per kilogram of total dry solids in the composition. Preferably, however, the dyes are incorporated in an amount of from $2\times10^{-3}$ to $3\times10^{-2}$ mole of acutance dye per kilogram of dry solids in the composition.

The light-sensitive compositions of the invention will normally be spread for use on a support, suitable supports including, for example, paper, polyester or polyamide film bases, and glass. The composition will normally be prepared as a solution or suspension which is spread as a layer on the support and then the solvent or vehicle is evaporated to leave a dry photosensitive layer. If desired, a coating aid or binder such as polyvinyl butyral, polymethyl methacrylate, cellulose acetate, polyvinyl acetate, cellulose acetate-propionate and cellulose acetate butyrate, can be incorporated in the light-sensitive mixture.

The substantially light-insensitive silver compound is suitably a silver salt of an organic acid. The organic acid can be a $C_{12}$ to $C_{29}$ aliphatic acid and is preferably a $C_{16}$ to $C_{25}$ aliphatic acid. Examples include silver behenate, silver laurate, silver myristate, silver palmitate, and silver stearate. Other silver salts of organic acids include silver arachidate and silver saccharine.

The reducing agent for this substantially light-insensitive silver compound can normally be quite mild. Suitable examples include hydroquinone and substituted phenols such as 1-methyl-4-hydroxy-naphthalene, methyl gallate, catechol, phenylene diamine, p-aminophenol and 1-phenyl-3-pyrazolidone. The reducing agent can be incorporated into the light-sensitive composition. Alternatively, the composition can be placed in contact with the reducing agent after exposure to light. For example, a light-sensitive coating can be exposed to a light image, placed in contact with a layer containing the reducing agent and the image then developed by heating. Preferably, however, the reducing agent is incorporated in the light-sensitive composition before this is spread on the support. Then the storage stability of the composition can be improved by incorporating in the composition a small amount of a stabilizer such as an acid stabilizer, e.g., succinic acid, benzoic acid or salicycilic acid.

The silver halide can be present in amounts of up to 20% by weight of the mixture of silver compounds or can be present in small amounts, e.g., 0.1 to 10% by weight of the mixture of silver compounds. It can be added as such to the substantially light-insensitive compound or formed in situ by adding a soluble halide, e.g., a mercury or sodium halide, to the substantially light-insensitive silver compound. The silver halide, can, for example, be chloride, bromide or a mixture of them and/or other silver halide.

The light-sensitive compositions of the invention can include one or more sensitizing dyes to improve their sensitivity to parts of the spectrum other than the shorter wavelengths. Thus dye sensitized dry silver compositions of the present invention can contain an additional acutance dye such as one of those described in U.S. patent application Ser. No. 896,439, filed Apr. 14, 1978.

The dyes of the present invention may all be made according to the following reaction scheme:

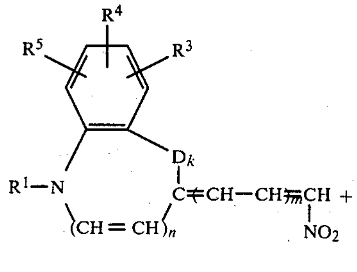

-continued

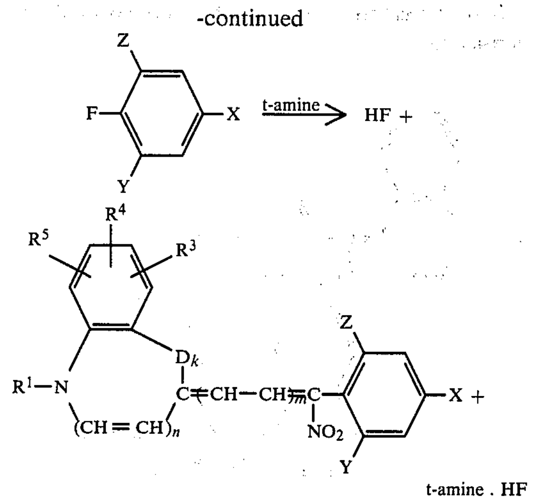

ps This method is performed in the presence of a strong tertiary amine such as a diisopropylethylamine. For example, in forming 1,4-dihydro-4-(2,4-dinitrophenyl)-nitromethylene-1-methylquinoline (which may be also named 1,4-dihydro-1-methyl-4-(α,2,4-trinitrobenzylidene)quinoline), one would react 4-nitromethylene-1-methyl-1,4-dihydroquinoline with 2,4-dinitrofluorobenzene in diisopropylethylamine. Referring to the preferred structural formula II, the following compounds were prepared by this method.

| Ex. No. | $R^6$ | $R^7$ | $R^8$ | X | Y | Melt. P. (°C.) (Decomposition Temperature) |
|---|---|---|---|---|---|---|
| 1 | $C_2H_5$ | H | H | $NO_2$ | $NO_2$ | 228-30 |
| 2 | $C_3H_7$ | H | H | $NO_2$ | $NO_2$ | 215 |
| 3 | $C_2H_5$ | H | H | CN | $NO_2$ | 232-4 |
| 4 | $CH_3$ | H | $CH_3$ | $NO_2$ | $NO_2$ | 237-9 |
| 5 | $C_2H_5$ | H | H | $NO_2$ (Z) | $NO_2$ | 230 |
| 6 | $CH_3$ | $OCH_3$ (4) | H | $NO_2$ | $NO_2$ | 205-06 |
| 7 | $CH_3$ | $OCH_3$ | H | CN | $NO_2$ | 229-31 |

In the table, the numbers in parentheses indicate the position of attachment for particular substituents. Infrared analysis and nucleus magnetic resonance analysis confirmed the structure of each of these dyes.

EXAMPLE 8

Four hundred grams of a dispersion containing 13 parts by weight of silver behenate in 87 parts of a solvent composed of 67 parts by weight methylethylketone, 26 parts by weight toluene, and 7 parts by weight methylisobutylketone was charged to a temperature-controlled stirred reaction vessel at 15° C. Dark room conditions were maintained during all subsequent work.

The following materials were added sequentially with 20–30 minutes of stirring between separate additions.

| | |
|---|---|
| A. | 2 g of 1-methyl-2-pyrrolidinone in 6 g of polyvinylbutyral, |
| B. | 8 ml of 2M HBr (in ethanol) and 3.2 ml of 0.1M HI (in ethanol) |
| C. | 10 g of a copolymer derived from 91% by weight vinylchloride, 3% vinylacetate, and 6% by weight vinyl alcohol polymerized to a molecular weight of about 23,000, and 24 g of polyvinyl butyral, |
| D. | 1.8 ml of 0.5M $HgBr_2$ (in ethanol) was added with 5 minutes of stirring, |

-continued

| | |
|---|---|
| E. | 5.2 g of phthalazinone and 7.8 g of 2,6-bis-(2'-hydroxy-3'-t-butyl-5'-methylbenzyl)-4-methylphenol, |
| F. | 2.8 ml of a sensitizer solution having 5 mg/ml of the sensitizer in N-methyl pyrrolidone, the sensitizer having the formula: |

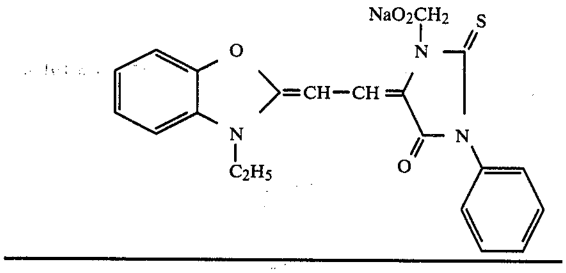

10 mg of each candidate acutance dye was weighed into separate vessels with 3 ml of methylethylketone to dissolve or disperse the dye. 50 gram portions of the light-sensitive dispersion formed above were combined with the dye solutions and to portions of methylethylketone alone as a control. All materials were stirred for three minutes. The portions were then allowed to stand at room temperature for 30 minutes, then they were knife coated at 85 microns thickness on polyester and dried for four minutes at 85° C. Each sample was top-coated with a 50 micron knife coating of a vinylchloride/vinylacetate copolymer as a 5% by weight solution in methylethylketone.

The produced film samples were exposed at the wavelengths indicated below through a 0.25 mm aperture mask overlaid with a continuous density wedge in a vacuum frame. This permitted an easy comparison of image flare at equivalent optical densities after development for 15 seconds at 127° C. in an inert fluorocarbon chemical bath. All dye samples had markedly less flare than the control samples, particularly at an optical density of 2.0. Except for the dye of Example 8, no samples left significant visible stain after processing. The dye of Example 8 left a magenta stain which faded within an hour under room light. The dyes used in the examples were as follows:

Example 8 (560 nm)

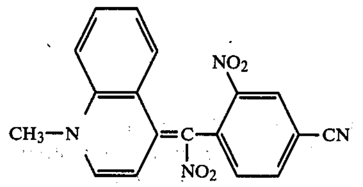

Example 9 (500 nm),

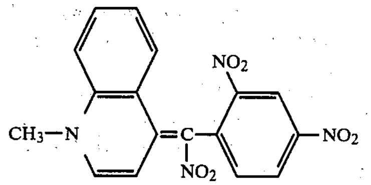

Example 10, the dye of Example 1 (500 nm),
Example 11, the dye of Example 2 (500 nm),
Example 12, the dye of Example 5 (500 nm).

What is claimed is:

1. A dye of the formula

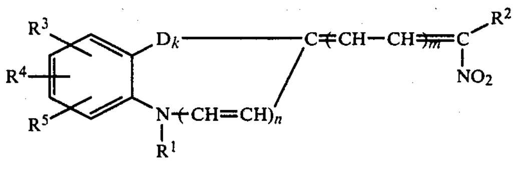

wherein $R^1$ is an alkyl group of from 1 to 12 carbon atoms, $R^2$ is the group

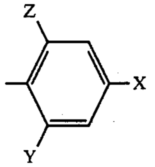

wherein X, Y, and Z are independently selected from the class consisting of H, $NO_2$, CN, perfluoroalkyl of 1 to 4 carbon atoms and halogen, with the proviso that at least one of X and Y is $NO_2$, $R^3$, $R^4$, and $R^5$ are independently selected from the group consisting of H, halogen, alkyl or alkoxy of 1 to 4 carbon atoms, alkenyl of 2 to 4 carbon atoms, $-(CH_2)_p$COOH wherein p is 0, 1, 2, or 3, $-NO_2$, $-NH_2$, or $-NHCOCH_3$, or any two of the adjacent groups are the atoms necessary to form a fused on benzene ring, D represents —HC=CH—, O, >$C(CH_3)_2$, —S—, —Se—, or >$NR^7$, $R^7$ represents an alkyl group of 1 to 4 carbon atoms or $CH_3CO$—, n is 1 when k is 0 and k is 1 when n is 0, and m is 0, 1, 2, or 3.

2. A dye according to claim 1 having the formula:

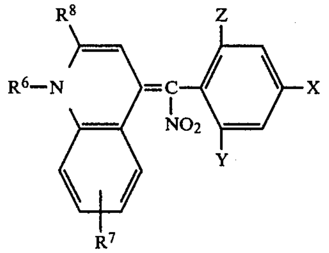

wherein $R^6$ is alkyl of 1 to 8 carbon atoms, $R^7$ is selected from the group consisting of alkyl, alkoxy, halogen, $NO_2$, and aryl, $R^8$ is selected from the group consisting of H, alkyl of 1 to 8 carbon atoms and alkoxy of 1 to 8 carbon atoms, and X, Y and Z are selected from the group consisting of H, $NO_2$, CN, halogen, and perfluoroalkyl of 1 to 4 carbon atoms with the proviso that at least one of X, Y and Z is $NO_2$.

3. The dye of claim 2 wherein $R^6$ is alkyl of 1 to 4 carbon atoms, $R^8$ is H, and X and Y are selected from the group consisting of $NO_2$ and CN, and Z is selected from the group consisting of H, $NO_2$, and CN.

4. The dye of claim 3 wherein X and Y are $NO_2$ and Z is H.

5. A dye according to claim 1 selected from the group consisting of

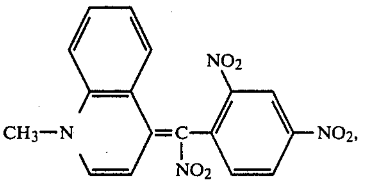

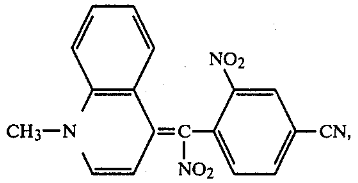

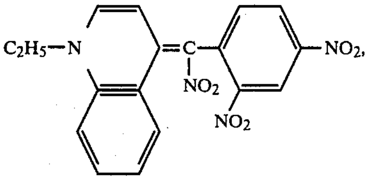

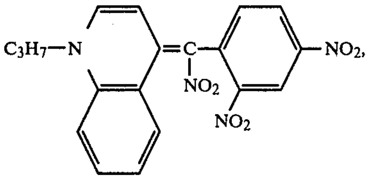

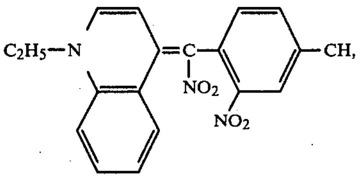

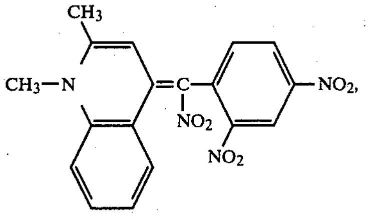

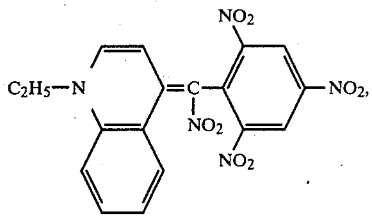

and

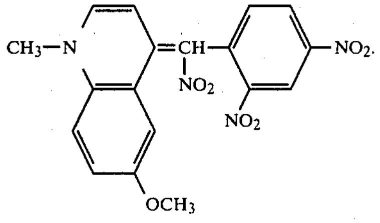

6. A dye according to claim 1 having the structure

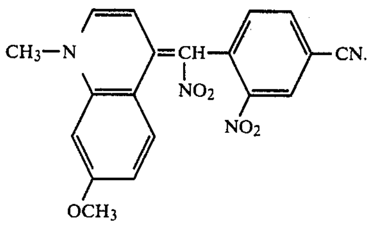
* * * * *
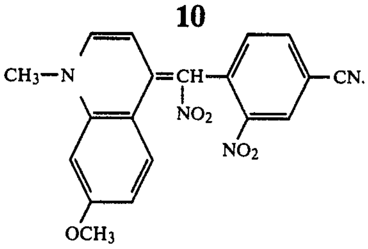
* * * * *

UNITED STATES PATENT AND TRADEMARK OFFICE

CERTIFICATE OF CORRECTION

PATENT NO. : 4,316,984

DATED : February 23, 1982

INVENTOR(S) : Harvey A. Brown

It is certified that error appears in the above—identified patent and that said Letters Patent is hereby corrected as shown below:

Column 10, claim 6, delete the second, identical structural drawing.

Signed and Sealed this

***Seventh* Day of *September 1982***

[SEAL]

*Attest:*

GERALD J. MOSSINGHOFF

*Attesting Officer* *Commissioner of Patents and Trademarks*